(12) United States Patent
Daly

(10) Patent No.: US 8,381,732 B2
(45) Date of Patent: Feb. 26, 2013

(54) NASAL INTERFACE DEVICE

(75) Inventor: Robert W. Daly, Providence, RI (US)

(73) Assignee: The Periodic Breathing Foundation, LLC, East Providence, RI (US)

( * ) Notice: Subject to any disclaimer, the term of this patent is extended or adjusted under 35 U.S.C. 154(b) by 973 days.

(21) Appl. No.: 12/383,316

(22) Filed: Mar. 23, 2009

(65) Prior Publication Data

US 2009/0250066 A1    Oct. 8, 2009

Related U.S. Application Data

(60) Provisional application No. 61/070,303, filed on Mar. 21, 2008.

(51) Int. Cl.
*A61M 15/08* (2006.01)
*A62B 7/00* (2006.01)

(52) U.S. Cl. ......... 128/207.18; 128/200.24; 128/206.11; 128/207.13

(58) Field of Classification Search ............. 128/200.24, 128/207.18, 206.11, 207.13
See application file for complete search history.

(56) References Cited

U.S. PATENT DOCUMENTS

| | | | |
|---|---|---|---|
| 2,809,633 A | 10/1957 | Sweringen et al. | |
| 2,921,581 A | 1/1960 | Sweringen et al. | |
| 3,357,426 A | 12/1967 | Cohen et al. | |
| 4,112,938 A | 9/1978 | Jeretin | 128/204.23 |
| 4,188,946 A | 2/1980 | Watson et al. | 128/204.22 |
| 4,265,235 A | 5/1981 | Fukunaga | 128/200.24 |
| 4,467,799 A | 8/1984 | Steinberg | 128/106.14 |
| 4,648,398 A | 3/1987 | Agdanowski et al. | 128/207.18 |
| 5,320,093 A | 6/1994 | Raemer | 128/203.12 |
| 5,540,219 A | 7/1996 | Mechlenburg et al. | 128/204.23 |
| 5,540,223 A | 7/1996 | Starr et al. | 128/205.25 |
| 5,647,345 A | 7/1997 | Saul | 128/201.23 |
| 5,676,133 A | 10/1997 | Hickle et al. | 128/205.12 |
| 5,755,225 A | 5/1998 | Hutson | 128/207.18 |
| 5,794,615 A | 8/1998 | Estes | 128/204.23 |
| 5,901,704 A | 5/1999 | Estes et al. | 128/204.23 |
| 5,918,598 A | 7/1999 | Belfer et al. | 128/206.25 |
| 6,003,511 A | 12/1999 | Fukunaga et al. | 128/202.27 |
| 6,009,871 A | 1/2000 | Kiske et al. | 128/204.21 |
| 6,079,771 A * | 6/2000 | Brandner et al. | 296/216.09 |
| 6,196,223 B1 | 3/2001 | Belfer et al. | 128/206.25 |
| 6,227,196 B1 | 5/2001 | Jaffe et al. | 128/200.26 |

(Continued)

FOREIGN PATENT DOCUMENTS

| | | |
|---|---|---|
| EP | 0861672 | 9/1998 |
| FR | 1555589 | 1/1969 |

(Continued)

OTHER PUBLICATIONS

The International Search Report and Written Opinion of PCT/US2009/001809 dated Jul. 23, 2009.

(Continued)

*Primary Examiner* — Lynne Anderson
*Assistant Examiner* — Bradley Philips
(74) *Attorney, Agent, or Firm* — Barlow, Josephs & Holmes, Ltd.

(57) ABSTRACT

A nasal interface device and a method of use are disclosed. The device includes a facial adaptor configured to be secured to the nose of a user and having two nostril pads having open channels configured to be inserted into nostrils of the user and a piercing/swivel adaptor configured to interact with the facial adaptor through the two nostril prongs. The piercing/swivel adaptor is further configured to be coupled to an airway tube, the airway tube is configured to supply air/gas to the user.

11 Claims, 8 Drawing Sheets

U.S. PATENT DOCUMENTS

| | | | |
|---|---|---|---|
| 6,298,848 B1 | 10/2001 | Skog | 128/204.18 |
| 6,306,098 B1 | 10/2001 | Orr et al. | 128/200.26 |
| 6,318,362 B1 | 11/2001 | Johnson | 128/200.24 |
| 6,341,606 B1 | 1/2002 | Bordewick et al. | 128/206.25 |
| 6,354,292 B1 | 3/2002 | Fisher | 128/203.12 |
| 6,363,933 B1 | 4/2002 | Berthon-Jones | 128/204.23 |
| 6,367,474 B1 | 4/2002 | Berthon-Jones et al. | 128/204.23 |
| 6,397,847 B1 | 6/2002 | Scarberry et al. | 128/206.24 |
| 6,439,231 B1 | 8/2002 | Fukunaga et al. | 128/207.14 |
| 6,467,477 B1 | 10/2002 | Frank et al. | 128/203.23 |
| 6,494,206 B1 | 12/2002 | Bergamaschi et al. | 128/206.24 |
| 6,584,977 B1 | 7/2003 | Serowski | 128/206.24 |
| 6,599,252 B2 | 7/2003 | Starr | 600/532 |
| 6,609,517 B1 | 8/2003 | Estes et al. | 128/204.23 |
| 6,612,308 B2 | 9/2003 | Stenzler et al. | 128/205.11 |
| 6,615,831 B1 | 9/2003 | Tuitt et al. | 128/204.18 |
| 6,622,725 B1 | 9/2003 | Fisher et al. | 128/204.21 |
| 6,629,527 B1 | 10/2003 | Estes et al. | 128/204.18 |
| 6,640,806 B2 | 11/2003 | Yurko | 128/204.23 |
| 6,752,150 B1 | 6/2004 | Remmers et al. | 128/204.18 |
| 6,752,151 B2 | 6/2004 | Hill | 128/204.18 |
| 6,799,570 B2 | 10/2004 | Fisher et al. | 128/200.24 |
| 6,851,429 B2 | 2/2005 | Bishop | 128/206.25 |
| 6,908,438 B2 | 6/2005 | Orr et al. | 600/532 |
| 6,948,499 B2 | 9/2005 | Griesbach et al. | 128/206.25 |
| 6,951,217 B2 | 10/2005 | Berthon-Jones | 128/204.23 |
| 7,017,577 B2 | 3/2006 | Matich | 128/206.14 |
| 7,073,501 B2 | 7/2006 | Remmers et al. | 128/204.18 |
| 7,077,138 B2 | 7/2006 | Bateman et al. | 128/206.14 |
| 7,255,107 B1 * | 8/2007 | Gomez | 128/207.13 |
| 2001/0035182 A1 | 11/2001 | Rubin et al. | 128/200.23 |
| 2002/0059933 A1 | 5/2002 | Jaffe et al. | 128/204.22 |
| 2002/0185129 A1 | 12/2002 | Fisher et al. | 128/203.25 |
| 2003/0217746 A1 | 11/2003 | Gradon et al. | 128/201.26 |
| 2004/0016433 A1 | 1/2004 | Estes et al. | 128/204.21 |
| 2004/0035422 A1 | 2/2004 | Truitt et al. | 128/204.18 |
| 2004/0059239 A1 | 3/2004 | Jaffe et al. | 600/529 |
| 2004/0144383 A1 | 7/2004 | Thomas et al. | 128/204.18 |
| 2004/0206354 A1 | 10/2004 | Fisher et al. | 128/204.23 |
| 2005/0015036 A1 | 1/2005 | Lutri et al. | 602/41 |
| 2005/0066976 A1 * | 3/2005 | Wondka | 128/207.18 |
| 2006/0005837 A1 | 1/2006 | Thornton | 128/205.25 |

FOREIGN PATENT DOCUMENTS

| | | |
|---|---|---|
| FR | 2827778 | 1/2003 |
| WO | WO 97/10869 | 3/1997 |
| WO | WO 98/34683 | 8/1999 |
| WO | WO 99/52581 | 10/1999 |
| WO | WO 00/45882 | 8/2000 |
| WO | WO 2007/130067 | 11/2007 |

OTHER PUBLICATIONS

Lorenzi-Filho, et al. (1999), "Effects of Inhaled Carbon Dioxide and Oxygen on CheyneStokes Respiration in Patients with Heart Failure", *American Journal of Respiratory and Critical Care Medicine*, 159:1490-1498.

Vesely, et al., "A simple, effective method for controlling end tidal $PCQ_2$, for MRI mapping of cerebrovascular reactivity", *The Isocapnia Research Laboratory*, http://www.isocapnia.com/Fine%20Control%20of%20PCO2%20and%20P02.htm.

Vesely, et al. (2003), "Isocapnic hyperpnoea accelerates recovery from isoflurane anaesthesia", *British Journal of Anaesthesia*, 91 6:787-92.

"Nasal airflow dynamics: mechanisms and response associated with an external nasal dilator strip," J.P. Kirkness, J.R. Wheatley and T.C. Amis, European Respiratory Journal 2000; 15:929-936.

"Reusable Silicone Rubber Seal Accessory Attachment for the Hans Budolph 7500 & 7600 Series Oro-Nasal Masks Improves Sealing in the Nose Area of the Mask," Sensa Seal™ User Application Instructions, 2 pgs.

Chin Strap Comparison, http//www.epapman.com/chnstrps.html, 19 pgs.

"Effect of jaw position and posture on forced inspiratory airflow in normal subjects and patients with obstructive sleep apnea," by S. Masumi et al., Chest 1996; 109: 1484-1489.

International Search Report and Written Opinion for PCT/US08/06612 dated Oct. 1, 2008.

International Search Report for PCT/US2007/009454 dated Nov. 27, 2009.

International Search Report for PCT/US03/37236 dated Sep. 7, 2004.

Notification Concerning Transmittal of International Preliminary Report on Patentability for PCT/US2007/009454 dated Oct. 30, 2008.

* cited by examiner

NASAL INTERFACE DEVICE

CROSS-REFERENCE TO RELATED APPLICATIONS

The present application claims priority to U.S. Patent Provisional Patent Application No. 61/070,303 to Daly, filed Mar. 21, 2008, and entitled "Nasal Interface Device", and incorporates its disclosure herein by reference in its entirety.

The present application also relates to U.S. patent application Ser. No. 11/405,948, filed on Apr. 17, 2006, U.S. patent application Ser. No. 11/787,854, filed on Apr. 17, 2007, and International Patent Application No. PCT/US2007/009454, filed on Apr. 17, 2007, the disclosures of which are incorporated herein by reference in their entireties.

BACKGROUND OF THE INVENTION

1. Field of the Invention

The present invention relates generally to treatment of breathing disorders. In particular, the present invention relates to a nasal interface device that is relatively small, lightweight, easy to use, and can be connectable to a breathing apparatus.

2. Background of the Invention

Sleep-disordered breathing ("SDB") includes all syndromes that pose breathing difficulties during sleep. These include obstructive sleep apnea ("OSA"), mixed sleep apnea ("MSA"), central sleep apnea ("CSA"), Cheyne-Stokes respiration ("CSR"), and others. Some form of SDB occurs in approximately 3-5% of the U.S. population.

Anatomical problems such as obesity or an abnormally narrow upper airway are known to cause obstructive forms of SDB, in which the airway is vulnerable to collapse as a result of fluid dynamic stresses imposed by breathing. These stresses produce collapse during sleep, especially during rapid-eye-movement ("REM") sleep, when there is a reduction in the tone of muscles holding the airway open. An appropriate interface is required in order to deliver continuous positive airway pressure ("CPAP") therapy, during which air pressure in the range of 4-25 cm $H_2O$ is delivered from a pressure generator, via delivery hosing, and through the interface in order to pressurize the airway so that it will resist such collapse. Various types of interfaces are known, including nasal masks covering and creating a seal with the skin surrounding the nose, oro-nasal masks covering and creating a seal with the skin surrounding the nose and mouth, and "nasal pillow" devices which directly engage the nares of the nose by inserting soft, expandable elastomer tubes just inside the entrance to the nostrils. Small leaks are acceptable in such devices, which in any case usually incorporate an exhalation orifice producing a fixed leak in the range of 30-50 liters per minute to provide bias flow for the pressure generator and to prevent rebreathing of exhaled gases.

Neurological difficulties in controlling levels of blood gases, such as carbon dioxide ("$CO_2$") and oxygen ("$O_2$"), are increasingly being recognized as important contributors to other forms of SDB. This is especially true of the "central" syndromes, MSA, CSA and CSR, which may account for as much as 20% of all SDB. Changes in the neurological system that control blood gases often produce cyclic fluctuations in blood gases, and thus, unsteady respiratory patterns that cause arousals from sleep. These changes are accompanied by spikes in blood pressure and release of stress hormones that can cause long-term damage to a number of organ systems. Additionally, some SDB syndromes involve not only fluctuations in levels of blood gases, but also abnormal average levels of blood gases. For example, low levels of dissolved $CO_2$ in arterial blood are frequently encountered in CSR, making the blood alkaline and posing a clinical problem. Therapies directed towards the central SDB syndromes may involve modulation of breathing gases or control of exhalation of carbon dioxide. These therapies are able to stabilize respiration and establish appropriate blood gas levels by restoring normal control of blood gases. When such therapies are in use, substantially leak-proof interfaces are required in order to permit careful control of the gases being exchanged between the therapy devices and the user. Leaks as small as one liter per minute, which would equate to the amount of flow that would pass through a hole as small as 1 millimeter in diameter, may negate the effects of the therapy. Thus, many conventional interface designs currently in use for delivery of CPAP therapy would not be suitable for use in treatment of the central SDB syndromes, and a much more secure interface design is needed for optimum therapy.

Respiratory interfaces typically provide gaseous substance(s) to a user in a variety of applications, including treatment of the above referenced illnesses, anesthesiology, and assistance in breathing.

Many respiratory therapies attempt to manage precisely the inhaled, mixed and exhaled gases for a user. This may be achieved through a tight seal between the interface and facial contours of the user. A tight seal may be necessary not only in order to provide precise control of gases exchanged with the user, but also to prevent escape of inhalational agents into ambient air where they may affect clinical personnel. For example, when a respiratory interface is utilized in treating complex sleep apnea, a closed system is required to control the amount of carbon dioxide that is exhaled by the user.

In the past, a tight seal has usually been achieved through the use of straps and harnesses to pull the interface tightly against the user's face. Since facial geometries vary, the amount of pressure applied to the skin by the interface will vary from place to place on the face, creating "hot spots" where pressure may be quite high. In some instances, the pressure may be high enough to prevent effective blood perfusion at the hot spots, causing long-term skin breakdown and damage to the face of the user. Therefore, it may be desirable to have an interface that conforms to a user's face and puts little or no positive pressure on the user's face while providing a sufficient seal.

The hoses and tubes associated with many respiratory therapies apply various torque forces to the interface, making it desirable for the interface to be sufficiently rigid or stiff to provide a stable physical platform to resist such forces, and to provide the user with the perception of security and stability of the interface and seal when in use. In the case of respiratory interfaces that create a seal by engaging the nares of the nose with nasal pillows, it is essential that the interface provide a geometrically stable platform to hold the nasal pillows securely in relationship to the nose, otherwise there is a risk that torque forces will cause one or both of the nasal pillows to disengage from the nare, creating a large air leak.

A competing concern to the rigidity of an interface is its ability to conform to user's individual facial features while providing comfort to the user. Compliance with continuous positive airway pressure therapy is reported to be less than 50% after one year, primarily as a result of interface discomfort. The ability of an interface to conform to a user's face comfortably is generally provided by a cushion. However, the cushion also serves to distribute forces applied to the interface such as pulling caused by the attached hoses and tubing, thereby limiting the degree of conformity with the face and the degree of comfort.

Further, conventional CPAP masks and other interface devices are bulky, heavy, and are difficult to operate. Thus, there is a need for a light-weight nasal interface device that can provide air-tight connection to a breathing apparatus and allow flexibility of movement to its user.

SUMMARY OF THE INVENTION

A nasal interface device and a method of use are disclosed. In some embodiments, the device includes a facial adaptor configured to be secured to the nose of a user and incorporating pads configured to be secured inside the nostrils of a user and further configured to extend into the interior of one or both nostrils of the user (for illustrative purposes and ease of description only, also referred to as "nostril pads"). Each nostril pad is configured to be manufactured from a soft, elastomeric material. In some embodiments, the pad is configured to conform to the interior geometry of the user's nostril and to substantially follow the typical interior architecture of the nostril, especially the inner curvature of the nostril, wherein the inner circumference of the nostril at approximately 2-3 millimeters inside the nostril is substantially greater than the inner circumference at the opening of the nostril. In some embodiments, the nostril pads further include pilot holes disposed in each nostril pad. Each pilot hole is configured to be pierced using an appropriately-sized tube or a "nostril prong" by placing the nostril prong through the pilot hole after the nostril pad is inserted into the nostril. Upon insertion into the user's nostril, the nostril prongs provide a breathing passage through which air could be inhaled and exhaled without excessive resistance by the user. In some embodiments, the nostril prongs can be configured to be coupled to a piercing/swivel adaptor configured to interact with a facial adaptor via the two nostril prongs. Insertion of the nostril prongs into the pilot holes in the facial adaptor would expand the soft nostril pads, causing them to flare out and form a tight seal with the inner wall of the nostril, thereby "locking" the facial adaptor into the nose and providing an airtight seal due to the larger diameter of the inside of the nostril relative to the opening of the nostril. The piercing/swivel adaptor is further configured to be coupled to an airway tube, the airway tube is configured to supply air/gas to the user.

In some embodiments, the present invention relates to a method of applying a nasal interface device to a nose of a user. The method includes securing a facial adaptor to the nose of the user, wherein the facial adaptor includes soft elastomeric nasal pads with pilot holes. The nasal pads are configured to be inserted into the nostrils of the user The method further includes inserting a piercing/swivel adaptor incorporating tubular nostril prongs through the pilot holes in order to lock the facial adaptor inside the nostrils and to establish an air channel, and coupling an airway tube to the piercing/swivel adaptor, wherein the airway tube is configured to supply air/gas to the user.

In some embodiments, the present invention relates to a nasal interface device having a facial adaptor configured to be secured to the nose of a user and having a nostril pad configured to be inserted into a nostril of the user. The nostril pad is configured to substantially conform to an interior geometry of the nostril upon insertion of the pad into the nostril and includes an open channel protruding through the nostril pad. A nostril tube is configured to be placed through the open channel in order to supply air/gas to the user.

In some embodiments, the present invention relates to a method of using a nasal interface device for supplying air/gas to a user. The method includes securing a facial adaptor to the nose of the user, wherein the facial adaptor includes a nostril pad configured to be inserted into a nostril of the nose of the user, the nostril pad is configured to substantially conform to an interior geometry of the nostril upon insertion of the pad into the nostril and includes an open channel protruding through the nostril pad. A nostril tube is configured to be placed through the open channel in order to supply air/gas to the user.

In some embodiments, the present invention relates to a nasal interface device having a facial adaptor configured to be secured to the nose of a user and having two nostril pads configured to be inserted into nostrils of the user, and a piercing/swivel adaptor configured to interact with the facial adaptor through the two nostril pads. The piercing/swivel adaptor is further configured to be coupled to an airway tube, the airway tube is configured to supply air/gas to the user.

In some embodiments, the present invention relates to a method of using a nasal interface device. The method includes securing a facial adaptor to the nose of the user, wherein the facial adaptor includes nostril pads configured to be inserted into nostrils of the user, inserting a piercing/swivel adaptor into the nostrils of the user through the nostril pads of the facial adaptor, and coupling an airway tube to the piercing/swivel adaptor, wherein the airway tube is configured to supply air/gas to the user.

In some embodiments, the present invention relates to a system for controlling breathing of a patient. The system includes a nasal interface device. The device includes a facial adaptor configured to be secured to the nose of a user and having two nostril pads configured to be inserted into nostrils of the user, a piercing/swivel adaptor configured to interact with the facial adaptor through the two nostril pads. The piercing/swivel adaptor is further configured to be coupled to an airway tube, the airway tube is configured to supply air/gas to the user.

Further features and advantages of the invention, as well as structure and operation of various embodiments of the invention, are disclosed in detail below will reference to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

In some embodiments, the present invention relates to a respiratory interface device that can be attached to the face of a user (or a patient) in order to allow the user to breathe through the device, where the device can be coupled to a breathing apparatus providing positive air pressure to the user.

Figure 1:
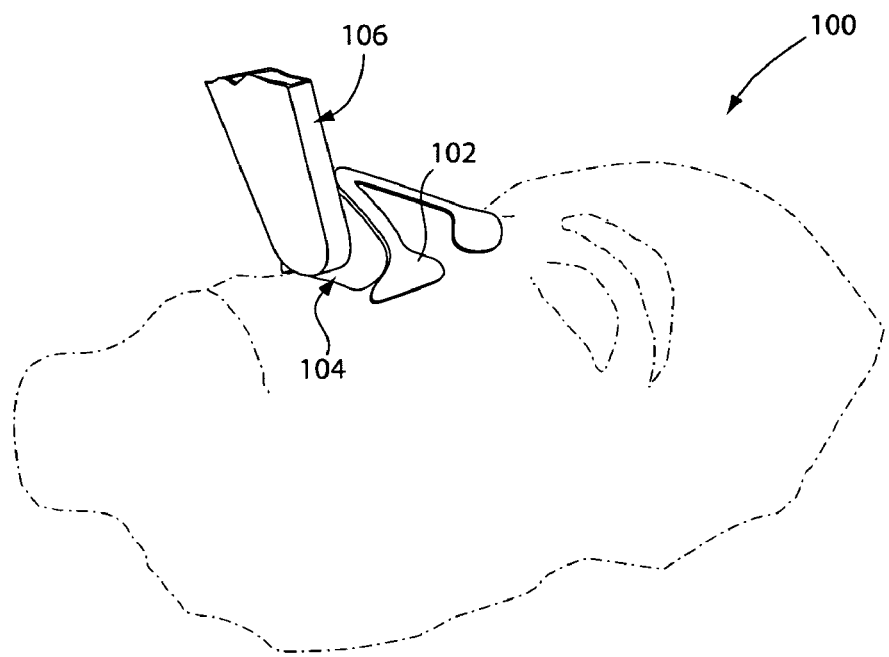
FIG. 1 illustrates an exemplary nasal interface device, according to some embodiments of the present invention.

FIG. 1 illustrates an exemplary nasal interface apparatus 100, according to some embodiments of the present invention. The nasal interface device 100 includes a facial adaptor 102 and a swivel/piercing element 104. The nasal interface device 100 is configured to be coupled to a swivel 106. The tubing 106 can be further coupled to a system for controlling breathing of a patient (not shown in FIG. 1), such as those described in the co-owned/co-pending U.S. patent application Ser. No. 11/405,948, filed on Apr. 17, 2006, U.S. patent application Ser. No. 11/787,854, filed on Apr. 17, 2007, and International Patent Application No. PCT/US2007/009454, filed on Apr. 17, 2007, the disclosures of which are incorporated herein by reference in their entireties.

Figure 2:
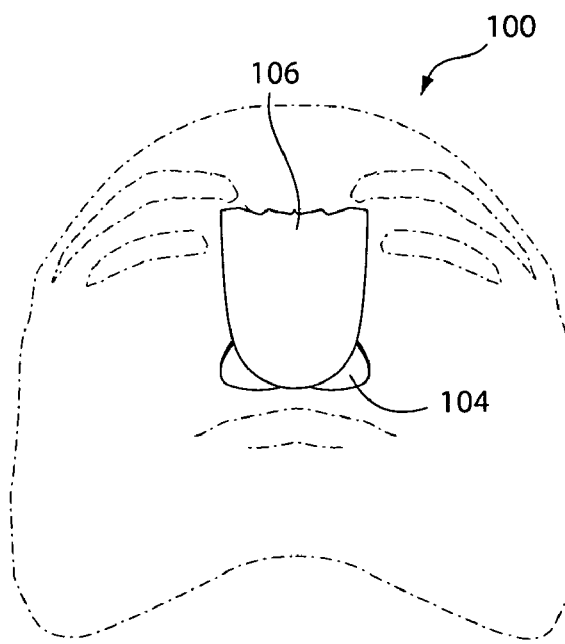
FIG. 2 is a side view from beneath the nose of the nasal interface device shown in FIG. 1.

FIG. 2 is a side view of the nasal interface apparatus 100 shown in FIG. 1. FIG. 2 further illustrates that the swivel/piercing element 104 allows the tubing 106 to rotate as the user moves his/her head (e.g., the user rolls to the side on his/her bed during sleep). In some embodiments, the tubing 106 is configured to be coupled to the system for controlling breathing (not shown in FIGS. 1 and 2) that can be discretely disposed above the user's head or away from sight to sustain an aesthetic appearance of the room and prevent formation of the tubing clutter around the user.

Figure 3:
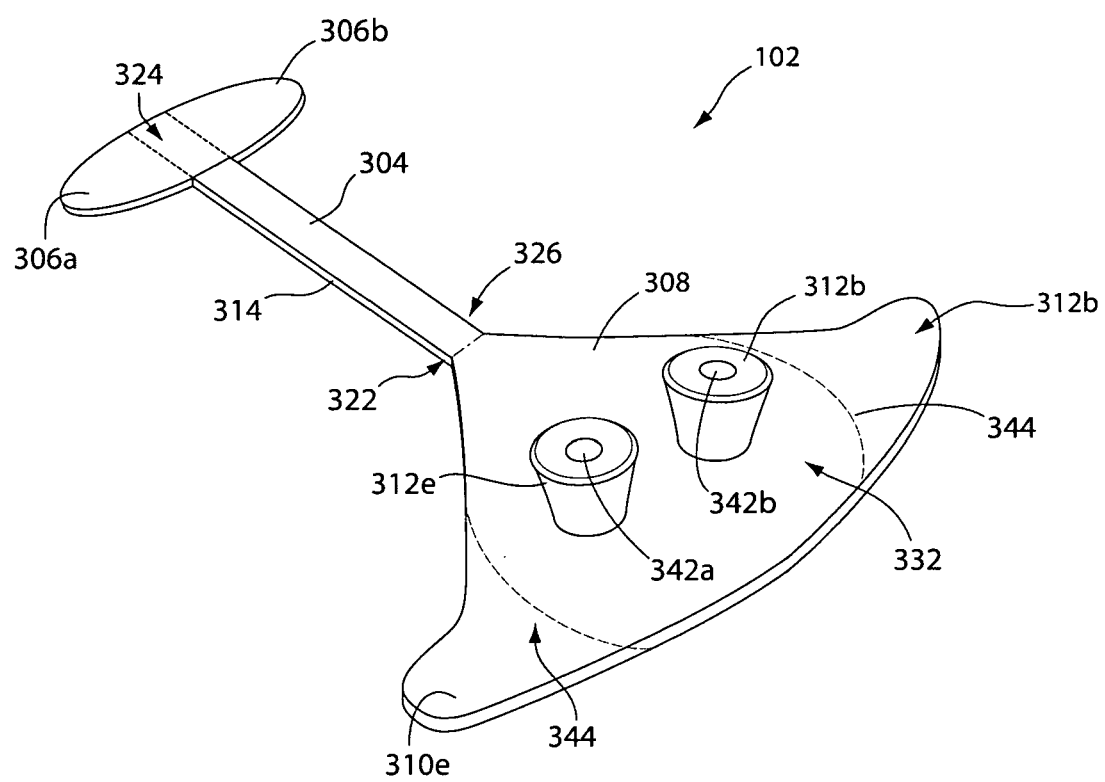
FIGS. 3-4 illustrate various views of an exemplary facial adaptor of the nasal interface device shown in FIG. 1, according to some embodiments of the present invention.
Figure 4:
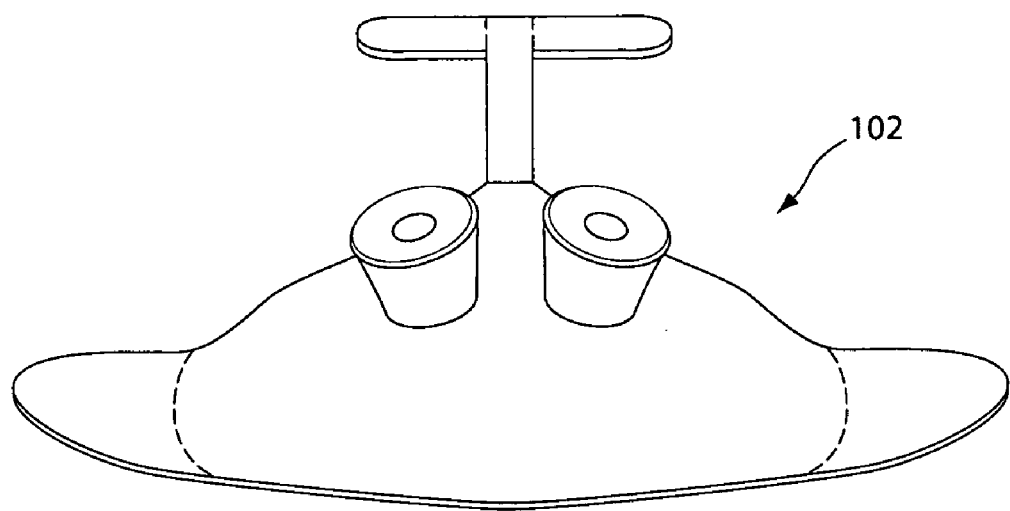
Figure 5:
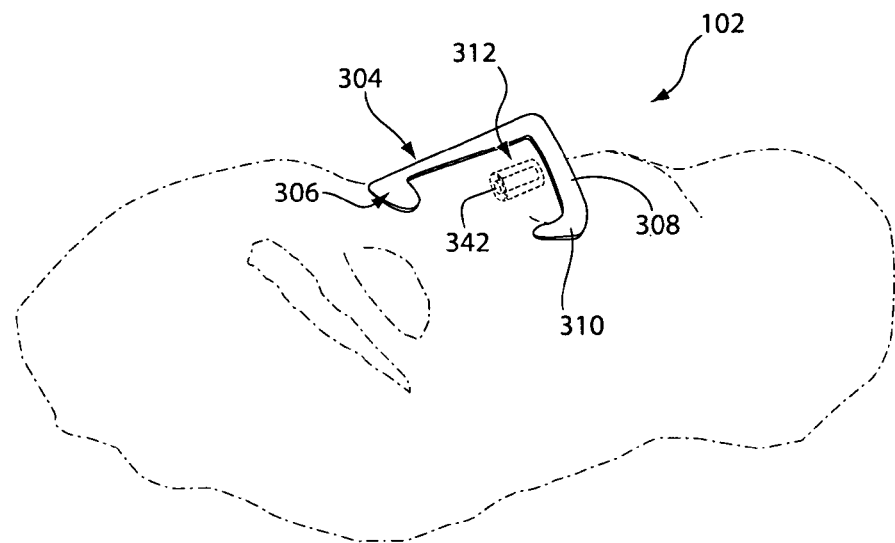
FIGS. 5-8 illustrate various views of the facial adaptor shown in FIGS. 3-4 being applied to the nose of the user.
Figure 6:
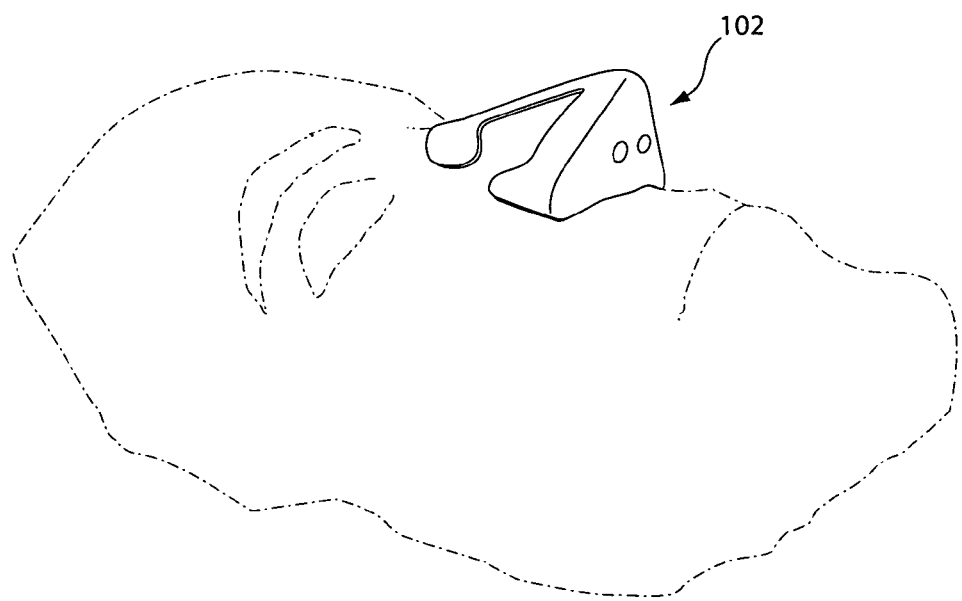
Figure 7:
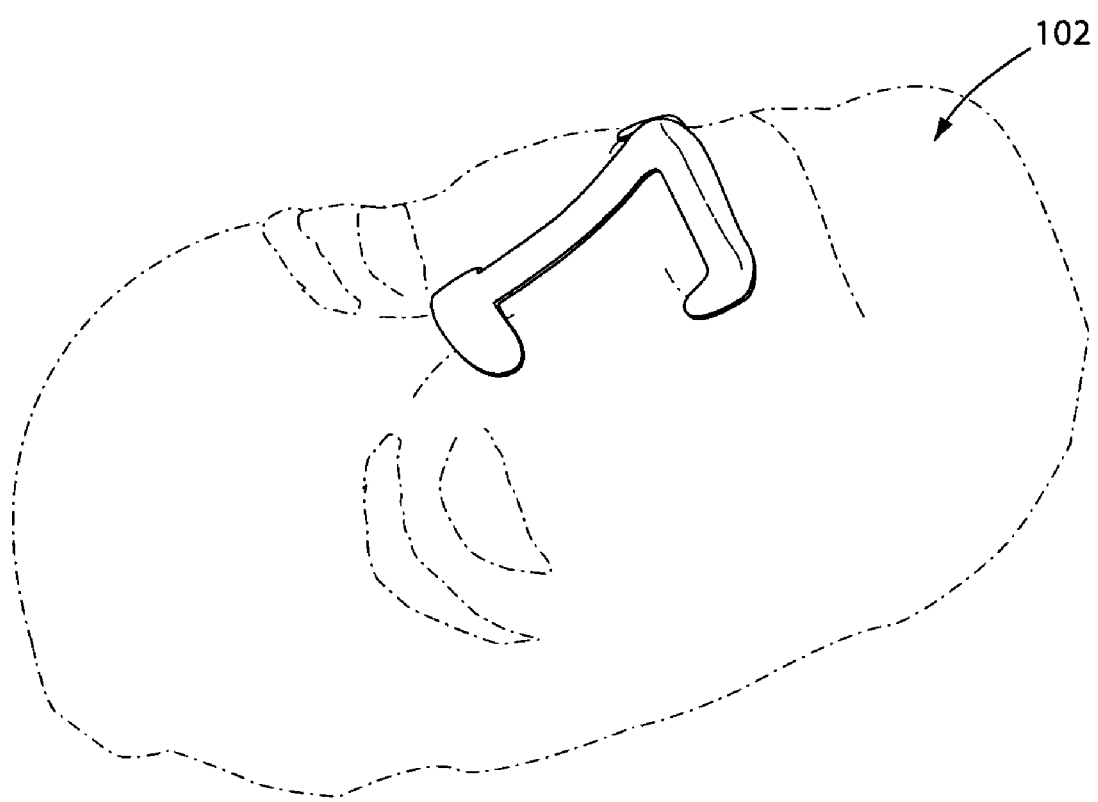
Figure 8:
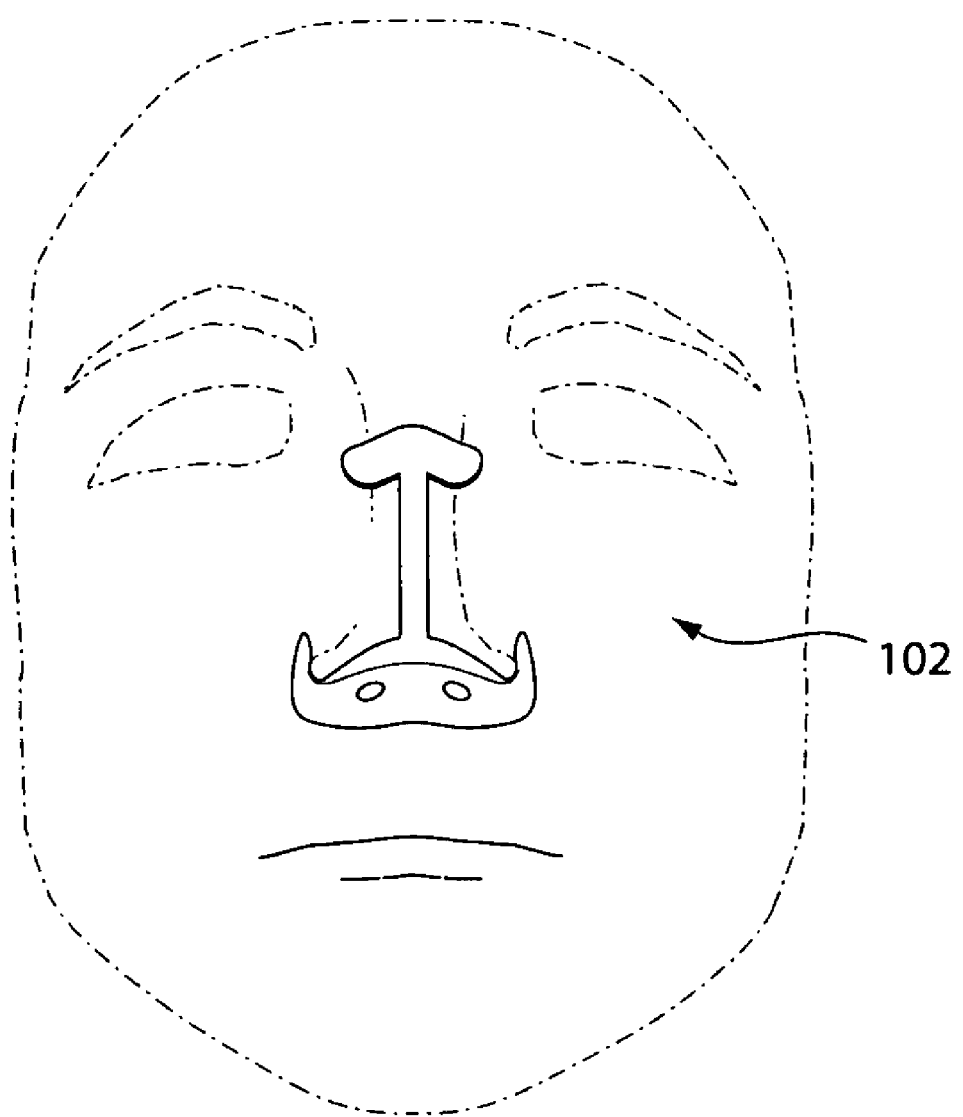

FIGS. 3-4 illustrate exemplary facial adaptor 102, according to some embodiments of the present invention. The facial adaptor 102 is configured to be coupled to the user's nose at various locations on the nose, as illustrated in FIGS. 5-8. The facial adaptor 102 includes nose attachment portions 304 and 308. The first portion 304 is configured to be attached to the bridge of the user's nose. The first portion 304 includes a strip 314 and side flaps 306a and 306b. The strip 314 includes a proximate end 322 and a distal end 324. The side flaps 306 are configured to be coupled at or substantially adjacent to the distal end 324 of the strip 314. The strip 314 is configured to be bendably coupled to the second portion 308 of the facial adaptor 102 at the bendable connection 326.

The side flaps 306 of the strip 314 are configured to bend around the axis of the strip 314. The side flaps 306 are configured to have a curved shape. The width, length, and height of the side flaps 306 are configured to accommodate the height of the bridge of the user's nose. The length of the strip 314 can be configured to accommodate length of bridge the user's nose. Thus, the present invention can be manufactured in way to accommodate child and adult users having varying facial parameters.

In some embodiments, the strip 314 and the side flaps 306 can be configured to include various means of attachment (shown in FIGS. 3-4) to allow further securing of the strip 314 and the flaps 306 to the nose of the user. In some embodiments, the strip 314 and the flaps 306 can be configured to form a friction clamp, whereby upon placement of the strip 314 and the flaps 306 on the bridge of the nose, the flaps 306 are bent toward the nose in a pinching-type motion, thus, gently squeezing the nose and preventing slippage of the facial adaptor 102 from the nose. In some embodiments, the flaps 306 can include various materials that can be configured to retain a certain shape once they are bent into a particular configuration and/or subject to a certain temperatures. In some embodiments, the flaps 306 can be configured to include any other means for attaching the flaps to the nose of the user, including but not limited to, adhesives, glue, friction devices, straps, or any other suitable devices. In some embodiments, the strip 314 is configured to be placed over the top of the bridge of the user's nose (or over the skin covering cartilage of the septum). The strip 314 is attached to the bridge of the user's nose in a way so that the proximate end 322 of the strip 314 is configured to coincide with the tip of the user's nose. Such attachment allows bending of the facial adaptor 102 at the bendable connection 326. Such attachment further allows the user to bend second portion 308 in a downward direction toward nasal airways of the user. Once the strip 314 is placed on the bridge of the user's nose, the side flaps 306 are forced in a downward direction toward the skin of the nose and are further attached to the nose as discussed above. As can be understood by one having ordinary skill in the art, the facial adaptor 102 can be manufactured from materials that can be configured to allow the adaptor 102 to retain a certain shape upon bending or twisting the adaptor 102 in a particular way.

The second portion 308 is configured to cover a bottom portion of the user's nose underneath the tip of the nose. In some embodiments, the second portion 308 can be shaped substantially similar to the bottom portion of the user's nose. In some embodiments, the second portion 308 has a substantially triangular shape. The second portion 308 has a substantially flat interior surface 332 that is configured to interact with the bottom portion of the nose. In some embodiments, the interior surface 332 is configured to cover the bottom edges of the user's nostrils upon adaptor 102 being installed on the user's nose. In some embodiments, the interior surface 332 can include glue, adhesives, friction-type devices, straps or any other types of mechanisms that are configured to further secure the facial adaptor 102 to the nose of the user. The second portion 308 further includes nostril pads, protrusions, or otherwise extensions (which will be referred to as "pads" in the following description) 312a and 312b. In some embodiments, the nostril pads 312 are configured to have substantially teardrop shape and protrude substantially vertically away from the interior surface 332. In some embodiments, the nostril pads 312 can be configured to protrude at an angle with regard to the interior surface 332. Further, the nostril pads 312 can be configured to have any desired shape. In some embodiments, the nostril pads 312 can be configured to create a substantially hermetic fit inside user's nostrils. As such, no air/gas can escape from the nostrils while the user is using the above device. As can be understood by one skilled in the art, the sizes of the nostril pads 312 can differ in order to accommodate varying size nostrils (e.g., children and adults). As can be further understood by one skilled in the art, the pads 312 can have any desired shape, including teardrop, cylindrical, oval, or any other suitable shape.

In some embodiments, the nostril pads 312 can be configured to have a greater diameter (or otherwise be larger) at the end distal from the interior surface 332 than the diameter of the nostril pads at the end proximate to the interior surface 332. This allows for the nostril pads to better conform to the interior geometry of the user's nose, whereby the diameter of a nostril may be greater at a point distal from the opening of the nostril than the diameter of the nostril at its opening.

In some embodiments, the nostril pads 312 include pilot holes 342 (a, b), respectively, formed along the axis of the nostril pads 312. The pilot holes 342 create open or pilot channels and allow insertion of tubes or nostril prongs disposed on the swivel/piercing element 104 (as shown and discussed below with regard to FIGS. 9a-c).

Side flaps 310(a) and 310(b) are coupled to the second portion 308 via bendable connections 344. As illustrated in FIG. 4, side flaps 310 are configured to fit immediately adjacent to the sides of the bottom of the nose of the user, e.g., along the side of the nose where the nose meets the face. Once the user places the facial adaptor 102 on the nose, the flaps 310 are configured to be bent up from the interior surface 332 of the adaptor 102 and be placed on the side of the user's nose in such a manner as to provide a clamping action that further secures adaptor 102 to the bottom portion of the nose. In some embodiments, the interior surface of side flaps 310 can be configured to include various means of attachment, including but not limited to, friction-type mechanisms and clamps, adhesives, glues, straps and any other suitable devices that that allow side flaps 310 to attach to the side of the nose.

In some embodiments, the facial adaptor 102 can be configured to be formed from a suitable biomedically compatible grade of soft elastomer such as polyurethane plastic. As can be understood by one skilled in the art, the facial adaptor 102 can be formed from any suitable material. Further, the facial adaptor 102 (with the exception of the nostril pads 312) can have a thickness on the order of 3-5 millimeters. In some embodiments, a friction-type mechanism, a glue, a thin-film adhesive, or any other suitable attachment means can be applied to the above-described parts of the facial adaptor 102. In some embodiments, the attachment means can be configured to create a non-permanent attachment to the skin of the user, thus, allowing the user to temporarily apply the facial adaptor 102 to user's face and remove it as necessary. Further, the attachment means can be such that same facial adaptor 102 can be removed from the user's face and then re-applied, e.g., the facial adaptor can use a repositionable attachment means that allows the user to remove and re-apply the adaptor. In some embodiments, the facial adaptor 102 can be a single or a multi-use device. In some exemplary embodiments, the weight of the facial adaptor 102 can be on order of 2 to 7 grams ("g").

The nostril pads 312 can be manufactured from a soft elastomeric material, such as medical grade polyurethane or any other suitable material. The elastomeric material can be configured to have a varying hardness coefficient that determines how flexible/hard this material can be. The hardness coefficient can be measured using a Shore-A scale having values between A 00, corresponding to the softest material, and A 100, corresponding to the hardest material. As can be understood by one skilled in the art, the nostril pads 312 can have a hardness coefficient in the range of approximately A 00 to approximately A 60. In some embodiments, the nostril pads 312 can be injection molded and attached (by any methods, including gluing, stapling, welding, thermo-gluing, or any other methods) to the interior surface 312 of the second portion 308. In some embodiments, the entire facial adaptor 102 can be manufactured from a single material, such as polyethylene, polyurethane, polyester, and any other plastic polymers.

The nostril pads 312 are configured to be disposed substantially in the center of the second portion 308 of the facial adaptor 102 and further match the location of user's nostrils so that upon insertion of the nostril pads 312 into the user's nostrils, the nostril pads 312 are comfortably disposed inside user's nostrils. In some embodiments, the nostril pads 312 can be disposed at an angle with regard to each other, as illustrated in FIGS. 3-4. With just the nostril pads 312 (i.e., without the breathing tubes or nostril prongs) being inserted into the user's nostrils, the user may be able to breathe through the nose. However, upon insertion of the breathing tubes, the nostril pads 312 expand inside the nostrils to provide a hermetic seal and, as stated above, do not allow leaking of air/gas between the interior walls of the nostrils and the pads.

In some embodiments, the nostril pads 312 can be used independently of the rest of adaptor 102 and configured to be individually inserted by the user into each nostril. In some embodiments, the nostril pads 312 can include a connector that connects the two pads 312. The connector allows the pads to be inserted into both nostrils simultaneously.

In order to put the facial adaptor 102 on the face, the user may perform the following steps. As discussed below, these steps may not necessarily be performed in the order that they are described. As can be understood by one skilled in the art, the steps can be performed in any order. In some embodiments, the user may first align the proximate end 322 of the first portion 304 with the tip of the user's nose and then apply the strip 314 along with wingtips 306 to the bridge and sides of the user's nose. Upon applying the strip 314 to the bridge of the user's nose, the wingtips 306 are bent in a downward direction and are applied to the sides of the user's nose. Then, the second portion 308 is bent in a downward direction toward the user's nostrils in order to cover the nose's airways. The nostril pads 312 are inserted into the nostrils. The side flaps 310 are then bent in an upward direction along the side of the user's nose. FIGS. 5-8 illustrate the facial adaptor 102 being placed over the user's nose.

In some embodiments, the facial adaptor 102 can be packaged by a manufacturer in a single-use sealed tray. The user would remove the adaptor 102 from the tray, (in embodiments using adhesives, the user also removes the adhesive liner covering the adhesive on the facial adaptor 102), then insert the nostril pads 312 into the user's nostrils, and then apply other portions of the facial adaptor 102 to the user's face (i.e., the first portion 304 is applied to the bridge of the user's nose and the side flaps 310 to the side of the user's nose).

In some embodiments, the strip 314 of the first portion 304 can be stiffened with laminated elastomer/PET structures. The bendable connections 326 and 344 as well as those between wingtips 306 and the strip 314 can be configured to be molded-in ridges that allow bending of the appropriate components of the facial adaptor 102. Further, the wingtips 306 as well as side flaps 310 can be configured to provide some squeezing force to the user's nose, when the facial adaptor 102 is applied to the nose, in order to further secure the adaptor 102 to the nose.

Figure 9A:
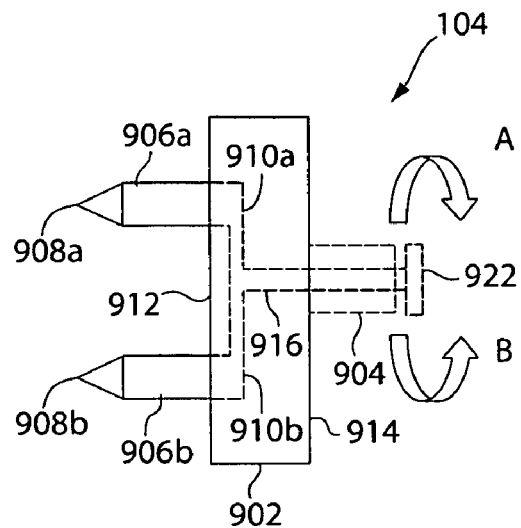
FIGS. 9a-c illustrate an exemplary piercing/swivel adaptor of the nasal interface device shown in FIG. 1, according to some embodiments of the present invention.
Figure 9B:
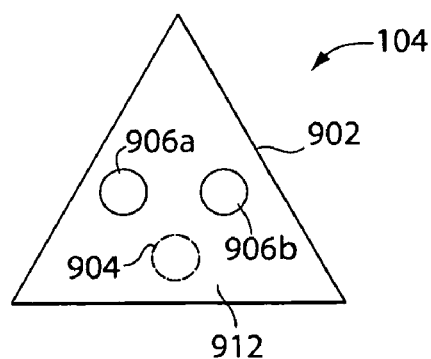
Figure 9C:
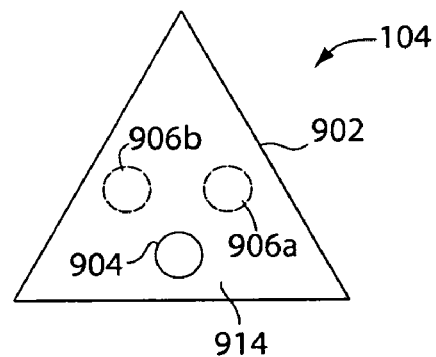

FIGS. 9a-c illustrate an exemplary swivel/piercing element 104, according to some embodiments of the present invention. The swivel/piercing element 104 includes a housing 902, nostril prongs or tubes 906(a, b), a connector tube 904, and a swivel adaptor 922. The housing 902 further includes an interior surface 912 and an exterior surface 914. The interior surface 912 is configured to interact with the facial adaptor 102 (not shown in FIGS. 9a-c). The exterior surface 914 is facing away from the user's nostrils. In some embodiments, the shape and size of the housing 902 is configured to conform to the shape and size of the second portion 308 of the facial adaptor 102 (now shown in FIGS. 9a-c) and can have a substantially triangular shape, as illustrated in FIGS. 9b and 9c. As can be understood by one skilled in the art, the element 104 can have any other desired shape and size.

The nostril tubes 906 are configured to protrude away from the interior surface 912. The tubes 906 are configured to be inserted into the openings or pilot holes 342 created in the nostril pads 312 (not shown in FIGS. 9a-c). Upon insertion of the nostril tubes 906, the tubes 906 are configured to push the elastomeric material of the nostril pads 312 away from the outer surface of the tubes 906 and toward the interior surfaces of the user's nostrils. By pushing the elastomeric material in such manner, the tubes 906 along with the nostril pads 312 are configured to create an air-tight seal in the nostrils, so that the only air/gas that is able to travel into the user's nose would go through the tubes 906 of element 104 and no air/gas can leak between the nostrils and the nostril pads 312.

The connector tube 904 is configured to protrude away from the exterior surface 914 of the housing 902. The tube 904 is configured to connect to the airway tube 106 (not shown in FIGS. 9a-c, but is shown in FIG. 1). To allow such connection, the tube 904 includes a swivel adaptor 922. The swivel adaptor 922 allows the airway tube 106 to rotate in any desired direction, as indicated by directional arrows A and B. Such rotation provides flexibility to the user, for example, when the user is rolling around in bed, walking around, or any performing any other activities.

The housing 902 and the tubes 906 and 904 are further configured to contain interior connector tubing 910 and 916 that connects tubes 906 and 904. Such interior connector tubing 910 and 916 provides airways from the user's nostrils through the tips 908, into the tubes 906, through the housing 902, into the tube 904, and then into the airway tube 106 (not shown in FIGS. 9a-c). When the nasal interface apparatus 100 is fully connected, as shown in FIGS. 1 and 2, the air/gas can travel to/from user's nostrils and into the airway tube 106. Alternatively, the housing 902 can be substantially hollow, providing an internal connection between the tubes 906 and 904. In some embodiments, the airway tube 106 can connected to a CPAP machine, as disclosed in co-owned/co-pending U.S. patent application Ser. No. 11/405,948, filed on Apr. 17, 2006, U.S. patent application Ser. No. 11/787,854, filed on Apr. 17, 2007, and International Patent Application No. PCT/US2007/009454, filed on Apr. 17, 2007, the disclosures of which are incorporated herein by reference in their entireties.

Figure 10:
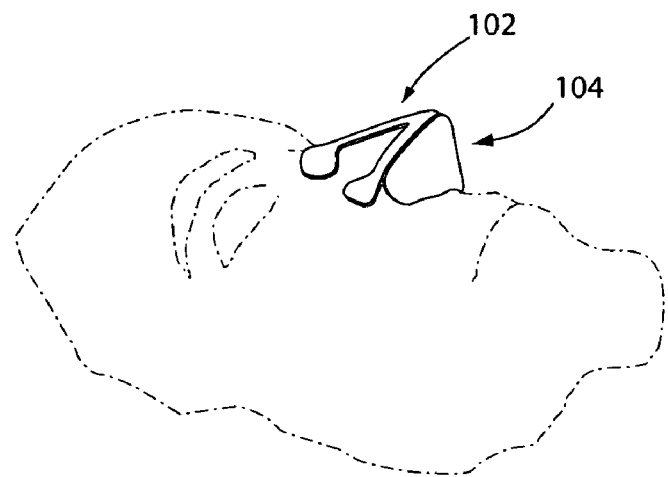
FIGS. 10-11 illustrate various views of the piercing/swivel adaptor shown in FIGS. 9a-c being applied to the nose of the user.
Figure 11:
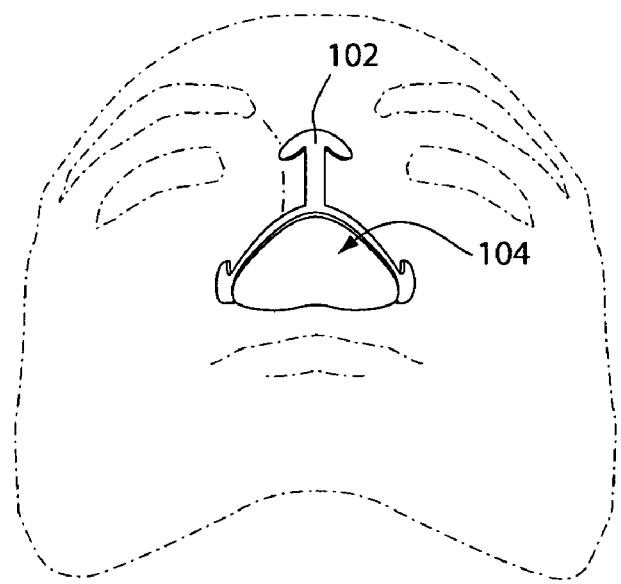

Referring to FIGS. 9a-c, once the user has attached the facial adaptor 102 to his/her nose, the element 104 is inserted, using its tubes 906, through the openings 342 (not shown in FIGS. 9a-c). FIGS. 10-11 illustrate such element 104 being coupled to the facial adaptor 102. The airway tube 106 can then be coupled to the swivel adaptor 922, as illustrated in FIGS. 1 and 2. As can be understood by one skilled in the art, this assembly can be disconnected at will. In some embodiments, the element 104 can be manufactured from a light, semi-rigid, Teflon material. As can be understood by one skilled in the art, the element 104 can be manufactured from any polyester, polyethylene, or any other polymer materials. The element 104 can be reusable or disposable. The swivel adaptor 922 can be any conventional swivel mechanism that allows rotation of the airway tube 106 once it is connected to the swivel adaptor 922.

In some embodiments, the thickness of the housing 902 can be on the order of 6-10 mm. Further, the length of the tubes 906 and 908 can be on the order of between approximately 4 mm to approximately 7 mm.

In some embodiments, each nostril pad 312 can be separately inserted into each respective nostril of the user, where nostril pads 312 are not attached to any external supporting devices, such as adaptor 102. In some embodiments, the nostril pads 312 can be configured to be coupled to a friction clamp or any other fixation device, which can be similar to the pads 306 being coupled to the first portion 304, that is configured to further secure the nostril pads 312 to the nose of the user. Additionally, in some embodiments, each one of the nostril prongs 906 can be configured to be separately inserted through the pilot holes 342 of the nostril pads without being coupled to the housing 902, i.e., each prong 906 can be coupled to a tube, which is further connected to an airway device. The prongs 906 are configured to create a locking arrangement inside the user's nostrils once the prongs 906 are inserted through the pilot holes 342.

In some embodiments, the present invention can be used in connection with a system for controlling breathing of a patient. The exemplary system includes the facial adaptor discussed above coupled to an airway device for supplying air/gas to the patient via an airway tube. Such system can be employed anywhere, including user's home, hospital, clinic, or any other facility. The system and/or the nasal interface device can be operated by the user himself/herself or a medical professional (e.g., doctor, nurse, etc.).

Example embodiments of the methods, circuits, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A nasal interface device, comprising:
 a facial adaptor including:
  a first portion comprising a bendable strip extending upwardly with bendable flaps extending outwardly therefrom, configured to be secured to the bridge of the nose of a user;
  a second portion forming a bottom thereof and configured to cover the bottom portion of the nose of a user; and
  nostril extensions affixed to said second portion and configured to be inserted into a nostril of the user, said nostril extensions are configured to substantially conform to an interior geometry of the nostril upon insertion of the extensions into the nostril and includes an open channel protruding through the nostril extensions; and
 a piercing/swivel adaptor including:
  nostril tubes including prongs that are inserted through said open channels in said nostril extensions causing said nostril pad to expand toward an interior surface of the nostril and form an air-tight seal between the nostril extension and the nostril;
  a swivel adaptor rotatably connected to said nostril tubes and further configured to be coupled to an airway tube configured to supply air/gas to the user.

2. The device according to claim 1, wherein said nostril extensions are configured to have a flared shape, whereby a distal end of the nostril extensions are configured to be inserted first into the nostril, has a greater diameter than a proximate end of the nostril end, configured to be disposed substantially adjacent to an opening of the nostril after insertion of said nostril extensions into the nostril;
 said flared shape of said nostril extensions is configured to create a locking arrangement with the nostril upon insertion of said nostril tube through said open channel of said nostril extensions.

3. The device according to claim 1, wherein said facial adaptor is configured to be externally affixed to the nose or the face of the user.

4. The device according to claim 3, further comprising a friction clamp coupled to said facial adaptor; wherein said friction clamp is configured to clamp the bridge of the nose of the user at least one side of the nose of the user.

5. The device according to claim 1, wherein said piercing/swivel adaptor comprises:
 a housing having an interior surface and an exterior surface;

said nostril tube configured to protrude away from said interior surface of said housing;

a connector tube configured to protrude away from said exterior surface of said housing;

said nostril tube is configured to be located on an opposite side of said housing as said connector tube;

said connector tube further includes a swivel element configured to allow connection of said airway tube;

said nostril tube and said connector tubes are configured to be connected to each other via an airway passage disposed inside said housing of said piercing/swivel adaptor.

6. The device according to claim 5, wherein upon insertion of said nostril tube into said open channel, the piercing/swivel adaptor is configured to create an airway passage between the nose of the user and the airway tube when the airway tube is coupled to said swivel element of said piercing/swivel adaptor.

7. The device according to claim 6, wherein said swivel element allows rotation of the airway tube when the airway tube is coupled to said swivel element.

8. The device according to claim 1, wherein said facial adaptor is manufactured from any biocompatible elastomeric material having a Shore A hardness rating in the range of Shore A 00 to Shore A 60.

9. The device according to claim 1, wherein said nostril extensions are manufactured from an elastomeric material.

10. The device according to claim 2, wherein said facial adaptor further comprises two nostril extensions, wherein each said nostril extension includes a respective open channel.

11. The device according to claim 10, wherein said piercing/swivel adaptor further comprises two nostril tubes configured to be inserted into each said respective open channel in said nostril extensions.

* * * * *